United States Patent [19]
Petri et al.

[11] Patent Number: 6,114,298
[45] Date of Patent: Sep. 5, 2000

[54] HARD SURFACE CLEANING AND DISINFECTING COMPOSITIONS COMPRISING ESSENTIAL OILS

[75] Inventors: Marco Petri, Angera Varese; Nicoletta Romano, Rome; Giadra Serego Allighieri, Rome; Marina Trani, Rome, all of Italy

[73] Assignee: The Procter & Gamble Company, Cincinnati, Ohio

[21] Appl. No.: 09/308,062

[22] PCT Filed: Nov. 6, 1997

[86] PCT No.: PCT/US97/20512

§ 371 Date: May 13, 1999

§ 102(e) Date: May 13, 1999

[87] PCT Pub. No.: WO98/21307

PCT Pub. Date: May 22, 1998

[30] Foreign Application Priority Data

Nov. 13, 1996 [EP]  European Pat. Off. .............. 96870146

[51] Int. Cl.$^7$ .............................. C11D 3/00; C11D 17/00; C11D 3/38
[52] U.S. Cl. .......................... 510/372; 510/463; 510/503; 510/506; 510/417
[58] Field of Search ..................................... 510/417, 365, 510/367, 372, 123, 370, 375, 463, 503, 506

[56] References Cited

U.S. PATENT DOCUMENTS

| | | | |
|---|---|---|---|
| 4,146,499 | 3/1979 | Rosano | 252/186 |
| 4,472,291 | 9/1984 | Rosano | 252/186.28 |
| 5,288,423 | 2/1994 | Behan et al. | 252/174.11 |
| 5,643,861 | 7/1997 | de Guertechin et al. | 510/365 |
| 5,665,268 | 9/1997 | de Guertechin et al. | 510/214 |
| 5,741,769 | 4/1998 | Erilli | 510/417 |

*Primary Examiner*—Necholus Ogden

[57] ABSTRACT

In its broadest embodiment the present invention relates to the use of a microemulsion comprising a surfactant, an aqueous phase and droplets dispersed in said aqueous phase, said droplets comprising an essential oil or an active thereof, and said droplets having a particle sized of less than 100 nanometers, for disinfecting a surface. The present invention further encompasses a microemulsion suitable for disinfecting a surface, comprising a surfactant, an aqueous phase comprising a bleach, and droplets dispersed in said aqueous phase, said droplets comprising an essential oil or an active thereof, and said droplets having a particle size of less than 100 nanometers.

17 Claims, No Drawings

HARD SURFACE CLEANING AND DISINFECTING COMPOSITIONS COMPRISING ESSENTIAL OILS

TECHNICAL FIELD

The present invention relates to compositions which can be used to disinfect various surfaces including animate surfaces (e.g., human skin, mouth and the like) and inanimate surfaces including, but not limited to, hard surfaces like walls, tiles, floors, glass, bathroom surfaces, kitchen surfaces, dishes as well as fabrics, clothes, carpets and the like.

BACKGROUND OF THE INVENTION

Antimicrobial/antibacterial compositions include materials which have the ability to disinfect. It is generally recognised that a disinfecting material greatly reduces or even eliminates the microorganisms, e.g., bacteria, existing on a surface. For example compositions based on quaternary ammonium compounds have been extensively described in the art for disinfecting purpose.

Although such disinfecting compositions provide acceptable disinfecting properties they do not encounter good acceptance amongst the consumers who are looking for disinfecting compositions based on safer and less harsh chemicals.

It is thus an object of the present invention to provide compositions which are effective disinfectants on various surfaces, and which are safe to the surfaces treated and the environment.

It has now been found that this can be achieved by formulating an essential oil or an active thereof in the form of a microemulsion having droplets dispersed in an aqueous phase, said droplets comprising said essential oil or an active thereof, and said droplets having a particle size of less than 100 nm. Indeed, it has surprisingly been found that improved disinfecting performance is provided with a microemulsion of the present invention, as compared to a similar composition which is not in the form of a microemulsion as defined in the present invention.

Thus, in its broadest embodiment the present invention encompasses the use of a microemulsion comprising a surfactant, an aqueous phase and droplets dispersed in said aqueous phase, said droplets comprising an essential oil or an active thereof, and said droplets having a particle size of less than 100 nanometers, for disinfecting a surface. The present invention also encompasses a microemulsion suitable for disinfecting a surface comprising a surfactant, an aqueous phase comprising a bleach, preferably a peroxygen bleach, and droplets dispersed in said aqueous phase, said droplets comprising an essential oil or an active thereof, and said droplets having a particle size of less than 100 nanometers.

An advantage of the present invention is that effective disinfecting performance is delivered on a broad range of bacterial strains including Gram positive and Gram negative bacterial strains but also more resistant micro-organisms like fungi, even at high dilution levels, e.g., up to dilution levels of from 1:100 (microemulsion:water).

Another advantage of the present invention is that besides the disinfection properties delivered, good cleaning is also provided as the microemulsions herein comprise at least one surfactant and optionally a solvent.

Also the microemulsions according to the present invention are suitable for disinfecting various surfaces including animate surfaces (e.g. human skin and/or mouth) as well as inanimate surfaces. Indeed, this technology is particularly suitable in hard-surfaces applications, laundry applications, e.g., in a so-called "soaking mode", "through the wash mode" and/or "pretreatment mode", as well as in carpet applications and the like.

BACKGROUND ART

WO 96/26262 discloses microemulsion light duty liquid cleaning compositions comprising 1% to 26% by weight of at least one anionic surfactant selected from the group consisting of sulfonate surfactants, alkyl sulfate surfactants and ethoxylated alkyl ether sulfate surfactants and mixtures thereof, 0% to 25% by weight of a zwitterionic surfactant, 0.5% to 29% by weight of a biodegradable compound selected from the group consisting of a mixture of an ethoxylated nonesterified polyhydric alcohol, an ethoxylated fully esterified polyhydric alcohol and an ethoxylated partially esterified polyhydric alcohol, 0.4% to 10% of a water insoluble hydrocarbon, essential oil or a perfume, 1% to 20% of a cosurfactant and the balance being water. No bleaches are disclosed. No disinfecting application is disclosed.

U.S. Pat. No. 5,468,725 discloses an alcohol-free transparent perfume consisting essentially of an alcohol-free perfume base, water and a stable transparent oil-in-water microemulsion fragrance concentrate consisting of water, at least one hydrophobic perfume oil (e.g., lavender oil, geraniol), at least one cationic surfactant and at least one non-ionic surfactant, wherein the transparent microemulsion perfume has a refractive index in the range of from 1.4 up to 1.6 at a temperature in the range of from 20° C. up to 30° C. No bleaches are disclosed. Also no disinfection application is disclosed.

WO 96/01305 discloses an aqueous cleaning composition which upon aqueous dilution by a factor of at least two produces a stable microemulsion, said emulsion having a measured dispersed phase particle size of 10–100 nanometers, said composition including water, surfactant (15%–40%), solvent (5%–30%), water insoluble oil (5%–20%), said composition having a measured dispersed phase particle size of greater than 100 nm prior to dilution. No bleaches are disclosed. No disinfection application is disclosed.

SUMMARY OF THE INVENTION

The present invention encompasses a microemulsion suitable for disinfecting a surface, comprising a surfactant, an aqueous phase comprising a bleach, and droplets dispersed in said aqueous phase, said droplets comprising an essential oil or an active thereof, and said droplets having a particle size of less than 100 nanometers.

In its broadest embodiment the present invention encompasses the use of a microemulsion comprising a surfactant, an aqueous phase and droplets dispersed in said aqueous phase, said droplets comprising an essential oil or an active thereof, said droplets having a particle size of less than 100 nanometers, for disinfecting a surface.

DETAILED DESCRIPTION OF THE INVENTION

Microemulsions of the Present Invention

The present invention encompasses a microemulsion suitable for disinfecting a surface comprising a surfactant, an aqueous phase comprising a bleach, and droplets dispersed in said aqueous phase, said droplets comprising an essential oil or an active thereof, and said droplets having a particle size of less than 100 nanometers.

The microemulsions of the present invention that may also be called "swollen micellar solutions" or "solubilized micellar solutions" have a transparent or translucent appearance, as opposed to an opaque or milk appearance typically associated with emulsions. The microemulsions herein are also physically stable. By "physically stable" it is meant herein that the microemulsions do not show phase separation upon prolonged storage, i.e., the droplets comprising essential oils/actives remain dispersed in the aqueous phase.

The present invention is based on the finding that improved disinfecting performance is provided when a disinfecting composition comprising a surfactant, a bleach preferably a peroxygen bleach, an essential oil or an active thereof and an aqueous phase is formulated in the form of a microemulsion comprising droplets dispersed in said aqueous phase, said droplets comprising said essential oil or an active thereof, and having a particle size of less than 100 nanometers, as compared to a similar composition which is not in the form of a microemulsion according to the present invention. Indeed, effective disinfecting performance is delivered with the microemulsions according to the present invention with a low total level of disinfecting actives.

By "effective disinfecting performance" it is meant herein that the microemulsions of the present invention allow to significantly reduce the amount of bacteria on an infected surface. Indeed, effective disinfection is obtained on various microorganisms including Gram positive bacteria like Staphylococcus aureus, and Gram negative bacteria like Pseudomonas aeruginosa, as well as on fungi like Candida albicans present on infected surfaces.

The disinfecting performance of a composition may be measured by the bactericidal activity of said composition. A test method suitable to evaluate the bactericidal activity of a composition on a surface is described in European Standard, prEN 1040, CEN/TC 216 N 78, dated November 1995 issued by the European committee for standardisation, Brussels. European Standard, prEN 1040, CEN/TC 216 N 78, specifies a test method and requirements for the minimum bactericidal activity of a disinfecting composition. The test is passed if the bacterial colonies forming units (cfu) are reduced from a $10^7$ cfu (initial level) to a $10^2$ cfu (final level after contact with the disinfecting product), i.e., a $10^5$ reduction of the viability is necessary. The microemulsions according to the present invention pass this test, even if used in highly diluted conditions, e.g. up to a dilution level of 100:1 (water:microemulsion).

Preferably in the microemulsions according to the present invention as is said droplets comprising said essential oil or active thereof, have a particle size of less than 90 nm, preferably less than 80 nm. Dilution upon use of the microemulsions of the present invention does not affect the particle size of said droplets inasmuch that the particle size of said droplets is less than 100 nm, preferably less than 90 nm upon dilution.

A test method suitable to evaluate the size of the droplets comprising said essential oil or an active thereof in the microemulsions according to the present invention is Cryo-transmission electron microscopy (Cryo-TEM). Cryo-TEM samples are prepared in a controlled environment vitrification system (CEVS) which is described in detail in Bellare, J. R.; Davis, H. T.; Scriven, L. E.; Talmon, Y., Controlled environment vitrification system (CEVS): An improved sample preparation technique, J. Electron Microsc. Tech., 1988, 10, 87–111. A 5 $\mu$l drop of the sample microemulsion is placed on a carbon-coated holey polymer support film mounted on the surface of a standard 200-mesh TEM grid (Ted Pella, Inc., Catalog # 01883). The drop is blotted with filter paper until it is reduced to a thin film (10–200 nm) of the sample spanning the holes (2–8 $\mu$m) of the support film. The sample is then vitrified by rapidly plunging it through a synchronous shutter at the bottom of the CEVS into liquid ethane at its freezing point. The vitreous specimen is transferred under liquid nitrogen into a Philips CM12® microscope for imaging. The temperature of the sample is kept under −170° C. throughout the examination.

An essential element of the present invention is an essential oil or an active thereof or mixtures thereof.

Suitable essential oils or actives thereof to be used in the microemulsions herein are those essential oils which exhibit antimicrobial activity and more particularly antibacterial activity. By "actives of essential oils" it is meant herein any ingredient of essential oils that exhibit antimicrobial/antibacterial activity. It is speculated that said essential oils and actives thereof act as proteins denaturing agents. A further advantage of said essential oils and actives hereof is that they impart pleasant odor to the microemulsions according to the present invention with out the need of adding a perfume. Indeed, the microemulsions according to the present invention deliver not only excellent disinfecting performance on infected surfaces but also good scent.

Such essential oils include, but are not limited to, those obtained from thyme, lemongrass, citrus, lemons, oranges, anise, clove, aniseed, cinnamon, geranium, roses, mint, lavender, citronella, eucalyptus, peppermint, camphor, sandalwood and cedar and mixtures thereof.

Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, terpineol, limonene, and mixtures thereof. Preferred actives of essential oil s to be used herein are thymol, eugenol, verbenone, eucalyptol, limonene and/or geraniol.

Thymol may be commercially available for example from Aldrich, eugenol may be commercially available for example from Sigma, Systems—Bioindustries (SBI)—Manheimer Inc.

Typically, the microemulsions according to the present invention comprise from 0.005% to 5% by weight of the total microemulsion of said essential oil or active thereof or mixtures thereof, preferably from 0.006% to 3%, more preferably from 0.05% to 1%.

Another essential element of the present invention is a surfactant or a mixture thereof.

A surfactant is needed in order to form the microemulsions according to the present invention because it allows to disperse the oily phase, i.e. droplets comprising the essential oil or an active thereof, in the aqueous phase of the oil-in-water microemulsions of the present invention. In other words, in the absence of any surfactant the present microemulsions would not form because the dispersed oily phase, i.e. the droplets comprising the essential oil or an active thereof, would tend to quickly grow and separate from the aqueous phase. Thus, the presence of a surfactant or mixtures thereof allows to control the size of the droplets comprising said essential oil or active thereof according to the present invention.

It is understood herein that the surfactant to be used herein or mixtures thereof as well as the levels thereof are chosen, depending on the nature and level of the essential oil or active thereof, so as to form the microemulsions according to the present invention.

Typically, the microemulsions according to the present invention comprise from 0.01% to 40% by weight of the total microemulsion of a surfactant, or mixtures thereof, preferably from 0.05% to 15% and more preferably from 0.1% to 12%.

Suitable surfactants to be used in the present invention include any surfactant known to those skilled in the art as being able to form a microemulsion as defined herein, comprising droplets comprising the essential oil or an active thereof, when adding to an aqueous composition comprising said essential oil or an active thereof. Suitable surfactants include nonionic, anionic, cationic, amphoteric and/or zwitterionic surfactants. Said surfactants are also desirable herein as they contribute to the cleaning performance of the present microemulsions.

Preferred surfactants to be used herein are the zwitterionic and/or amphoteric surfactants.

Suitable amphoteric surfactants to be used herein include amine oxides having the following formula $R_1R_2R_3NO$ wherein each of R1, R2 and R3 is independently a saturated substituted or unsubstituted, linear or branched hydrocarbon chains of from 1 to 30 carbon atoms. Preferred amine oxide surfactants to be used according to the present invention are amine oxides having the following formula $R_1R_2R_3NO$ wherein R1 is an hydrocarbon chain comprising from 1 to 30 carbon atoms, preferably from 6 to 20, more preferably from 8 to 16, most preferably from 8 to 12, and wherein R2 and R3 are independently substituted or unsubstituted, linear or branched hydrocarbon chains comprising from 1 to 4 carbon atoms, preferably from 1 to 3 carbon atoms, and more preferably are methyl groups. R1 may be a saturated substituted or unsubstituted linear or branched hydrocarbon chain.

Suitable amine oxides for use herein are for instance natural blend C8–C10 amine oxides as well as C 12–C 16 amine oxides commercially available from Hoechst.

Amine oxides are preferred herein as they deliver effective cleaning performance and further participate to the disinfecting properties of the microemulsions herein.

Suitable zwitterionic surfactants to be used herein contain both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylates and sulfonates, although other groups like sulfates, phosphonates, and the like can be used. A generic formula for some zwitterionic surfactants to be used herein is

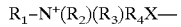

wherein $R_1$ is a hydrophobic group; $R_2$ and $R_3$ are each $C_1$–$C_4$ alkyl, hydroxy alkyl or other substituted alkyl group which can also be joined to form ring structures with the N; $R_4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group. Preferred hydrophobic groups $R_1$ are alkyl groups containing from 1 to 24, preferably less than 18, more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Highly preferred zwitterionic surfactants include betaine and sulphobetaine surfactants, derivatives thereof or mixtures thereof. Said betaine or sulphobetaine surfactants are preferred herein as they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g., delicate laundry or surfaces in contact with food and/or babies. Betaine and sulphobetaine surfactants are also extremely mild to the skin and/or surfaces to be treated.

Suitable betaine and sulphobetaine surfactants to be used herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants herein are according to the formula

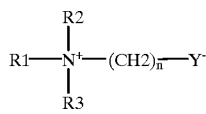

wherein R1 is a hydrocarbon chain containing from 1 to 24 carbon atoms, preferably from 8 to 18, more preferably from 12 to 14, wherein R2 and R3 are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of R1, R2 and R3 hydrocarbon chains is from 14 to 24 carbon atoms, or mixtures thereof.

Examples of particularly suitable betaine surfactants include C12–C18 alkyl dimethyl betaine such as coconutbetaine and C10–C16 alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Other specific zwitterionic surfactants have the generic formulas:

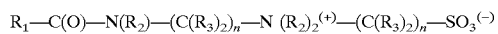

or

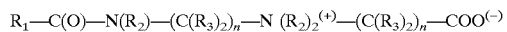

wherein each $R_1$ is a hydrocarbon, e.g. an alkyl group containing from 8 up to 20, preferably up to 18, more preferably up to 16 carbon atoms, each $R_2$ is either a hydrogen (when attached to the amido nitrogen), short chain alkyl or substituted alkyl containing from one to 4 carbon atoms, preferably groups selected from the group consisting of methyl, ethyl, propyl, hydroxy substituted ethyl or propyl and mixtures thereof, preferably methyl, each $R_3$ is selected from the group consisting of hydrogen and hydroxy groups and each n is a number from 1 to 4, preferably from 2 to 3, more preferably 3, with no more than one hydroxy group in any $(C(R_3)_2)$ moiety. The $R_1$ groups can be branched and/or unsaturated. The $R_2$ groups can also be connected to form ring structures. A surfactant of this type is a $C_{10}$–$C_{14}$ fatty acylamidopropylene(hydroxypropylene)sulfobetaine that is available from the Sherex Company under the trade name "Varion CAS sulfobetaine" ®.

In a preferred embodiment of the present invention where the microemulsions herein are particularly suitable for the disinfection of a hard-surface, the surfactant is typically a surfactant system comprising an amine oxide and a betaine or sulphobetaine surfactant, preferably in a weight ratio of amine oxide to betaine or sulphobetaine of 1:1 to 100:1, more preferably of 6:1 to 100:1 and most preferably 10:1 to 50:1. The use of such a surfactant system in the microemulsions herein particularly suitable for disinfecting a hard-surface, provides effective cleaning performance and provides shine on the cleaned surfaces, i.e., the amount of filming/streaking left on the cleaned surface that has been treated with said microemulsions is minimal.

Suitable nonionic surfactants to be used herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are the hydrophobic nonionic surfactants having an HLB (hydrophilic-lipophilic balance) below 16 and more preferably below 15. Those hydrophobic nonionic surfactants have been found to provide good grease cutting properties.

Preferred nonionic surfactants to be used in the microemulsions according to the present invention are surfactants according to the formula RO-$(C_2H_4O)_n(C_3H_6O)_mH$, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the $C_8$ to $C_{22}$ alkyl chains. Accordingly, suitable hydrophobic nonionic surfactants for use herein are Dobanol$^R$ 91-2.5 (HLB=8.1; R is a mixture of C9 and $C_{11}$ alkyl chains, n is 2.5 and m is 0), or Lutensol $^R$ TO3 (HLB=8; R is a $C_{13}$ alkyl chains, n is 3 and m is 0), or Lutensol $^R$ AO3 (HLB=8; R is a mixture of $C_{13}$ and $C_{15}$ alkyl chains, n is 3 and m is 0), or Tergitol$^R$ 25L3 (HLB=7.7; R is in the range of $C_{12}$ to $C_{15}$ alkyl chain length, n is 3 and m is 0), or Dobanol$^R$ 23-3 (HLB=8.1; R is a mixture of $C_{12}$ and $C_{13}$ alkyl chains, n is 3 and m is 0), or Dobanol $^R$ 23-2 (HLB=6.2; R is a mixture of $C_{12}$ and $C_{13}$ alkyl chains, n is 2 and m is 0), or Dobanol $^R$ 45-7 (HLB=11.6; R is a mixture of $C_{14}$ and $C_{15}$ alkyl chains, n is 7 and m is 0) Dobanol $^R$ 23-6.5 (HLB=1 1.9; R is a mixture of $C_{12}$ and $C_{13}$ alkyl chains, n is 6.5 and m is 0), or Dobanol $^R$ 25-7 (HLB=12; R is a mixture of $C_{12}$ and $C_{15}$ alkyl chains, n is 7 and m is 0), or Dobanol$^R$ 91-5 (HLB=11.6; R is a mixture of $C_9$ and $C_{11}$ alkyl chains, n is 5 and m is 0), or Dobanol $^R$ 91-6 (HLB=12.5; R is a mixture of $C_9$ and $C_{11}$ alkyl chains, n is 6 and m is 0), or Dobanol $^R$ 91-8 (HLB=13.7; R is a mixture of $C_9$ and $C_{11}$ alkyl chains, n is 8 and m is 0), Dobanol $^R$ 91-10 (HLB=14.2; R is a mixture of $C_9$ to $C_{11}$ alkyl chains, n is 10 and m is 0), or mixtures thereof. Preferred herein are Dobanol$^R$ 91-2.5, or Lutensol$^R$ TO3, or Lutensol$^R$ AO3, or Tergitol $^R$ 25L3, or Dobanol $^R$ 23-3, or Dobanol $^R$ 23-2, or Dobanol $^R$ 23-10, or mixtures thereof. These Dobanol$^R$ surfactants are commercially available from SHELL. These Lutensol$^R$ surfactants are commercially available from BASF and these Tergitol $^R$ surfactants are commercially available from UNION CARBIDE.

Suitable anionic surfactants to be used herein include water soluble salts or acids of the formula ROSO$_3$M wherein R is preferably a $C_6$–$C_{24}$ hydrocarbyl, preferably an alkyl or hydroxyalkyl having a $C_8$–$C_{20}$ alkyl component, more preferably a $C_8$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethylammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenyl-ether-sulphonates and alkyl-carboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,052,179, $C_8$–$C_{24}$ alkylpolyglycolethersulfates (containing up to 10 moles of ethylene oxide); alkyl ester sulfonates such as $C_{14–16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula RO(CH$_2$CH$_2$O)$_k$CH$_2$COO-M$^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use in the microemulsions herein are the alkyl benzene sulfonates, alkyl sulfates, alkyl alkoxylated sulfates, paraffin sulfonates and mixtures thereof.

The aqueous phase of the microemulsions of the present invention comprises at least water and a bleach. Said aqueous phase may further comprise any other water-miscible ingredient desired in the microemulsions herein that has a higher affinity toward said aqueous phase than towards the essential oil/active-containing droplets dispersed therein.

Typically, the microemulsions according to the present invention comprise from 60% to 99.5% by weight of the total microemulsion of water, preferably from 80% to 99% and more preferably from 85% to 98%.

The aqueous phase of the microemulsions of the present invention comprises a bleach or a mixture thereof, as an essential ingredient.

Any bleach known to those skilled in the art may be suitable to be used herein including any chlorine bleach as well as any peroxygen bleach.

Suitable chlorine bleaches to be used herein include any compound capable of releasing chlorine when said compound is in contact with water. Suitable chlorine bleaches include alkali metal dichloroisocyanurates as well as alkali metal hypohalites like hypochlorite and/or hypobromite. Preferred chlorine bleaches are alkali metal hypochlorites. Various forms of alkali metal hypochlorite are commercially available like for instance sodium hypochlorite.

Preferred bleaches for use herein are peroxygen bleaches, more particularly hydrogen peroxide, or a water soluble source thereof, or mixtures thereof. Hydrogen peroxide is most preferred to be used in the microemulsions according to the present invention.

Peroxygen bleaches like hydrogen peroxide are preferred herein as they are generally perceived to be environmentally acceptable. For example the decomposition products of hydrogen peroxide are oxygen and water. Also, it is believed that the presence of said peroxygen bleach, especially hydrogen peroxide, in the microemulsions of the present invention contribute to the disinfection properties of said microemulsions.

As used herein a hydrogen peroxide source refers to any compound which produces perhydroxyl ions when said compound is in contact with water. Suitable water-soluble sources of hydrogen peroxide for use herein include percarbonates, persilicate, persulphate such as monopersulfate, perborates, peroxyacids such as diperoxydodecandioic acid (DPDA), magnesium perphthalic acid, dialkylperoxides, diacylperoxides, preformed percarboxylic acids, organic and inorganic peroxides and/or hydroperoxides and mixtures thereof.

Typically, the microemulsions herein comprise from 0.001% to 15% by weight of the total microemulsion of said bleach or mixtures thereof, preferably from 0.1% to 10%, and more preferably from 0.2% to 5%.

The aqueous microemulsions according to the present invention have a pH as is of from 1 to 12, preferably from 3 to 10, and more preferably from 3 to 9. The pH of the microemulsions can be adjusted by using alkalinising agents or acidifying agents. Examples of alkalinising agents are alkali metal hydroxides, such as potassium and/or sodium hydroxide, or alkali metal oxides such as sodium and/or potassium oxide. Examples of acidifying agents are organic or inorganic acids such as sulfuric acid.

The microemulsions of the present invention may comprise as a preferred optional ingredient, a hydroxylated solvent or a mixture thereof.

Such hydroxylated solvents are suitable herein because they assist/promote the formation of the microemulsions of the present invention on top of the surfactants herein, and thus further contribute to control the size of the droplets comprising an essential oil or an active thereof, and being dispersed in the aqueous phase of the microemulsions of the present invention. Such hydroxylated solvents will at least partially be present in the oily phase of the oil-in-water microemulsions of the present invention, i.e., in the droplets comprising the essential oils/actives.

By "hydroxylated solvent" it is meant herein any hydrocarbon including aliphatic saturated or unsaturated hydrocarbons or aromatic hydrocarbons comprising at least one hydroxyl group (OH). Suitable hydroxylated solvents include glycol ethers and/or derivatives thereof, polyols, alkoxylated aliphatic or aromatic alcohols, aliphatic or aromatic alcohols, glycols or mixtures thereof.

Suitable glycol ethers and/or derivatives thereof to be used herein include monoglycol ethers and/or derivatives thereof, di-, tri- and poly-glycol ethers and/or derivatives thereof and mixtures thereof.

Suitable monoglycol ethers and derivatives thereof to be used herein include propylene glycol butyl ether, and water-soluble CELLOSOLVE® solvents or mixtures thereof. Preferred Cellosolve® solvents include 2-(Hexyloxy)ethanol (i.e., 2-hexyl Cellosolve®), ethylene glycol ethyl ether (i.e., 2-ethyl Cellosolve®), ethylene glycol butyl ether (i.e., 2-butyl Cellosolve ®) or mixtures thereof.

Suitable polyglycol ethers and derivatives thereof to be used herein include n-butoxypropoxypropanol (n-BPP), butyl triglycol ether (BTGE), butyl diglycol ether (BDGE), diethylene glycol butyl ether, water-soluble CARBITOL® solvents or mixtures thereof.

Preferred water-soluble CARBITOL® solvents are compounds of the 2-(2-alkoxyethoxy)ethanol class, 2-(2-alkoxyethoxy)propanol class and/or 2-(2-alkoxyethoxy) butanol class wherein the alkoxy group is derived from ethyl, propyl, butyl and tert-butyl. A preferred water-soluble carbitol is 2-(2-butoxyethoxy)ethanol also known as butyl carbitol®.

Suitable polyols to be used herein are aliphatic linear or branched saturated or unsaturated hydrocarbons having from 2 to 12 carbon atoms, preferably 4 to 10, and comprising at least 2 hydroxyl groups, preferably from 2 to 4. Suitable polyols herein are diols such as 2-ethyl-1,3-hexanediol, 2,2,4-trimethyl-1,3-pentanediol, methyl-2,4 pentanediol, 1,6-hexanediol or mixture thereof.

Suitable alkoxylated aliphatic or aromatic alcohols to be used herein are according to the formula R $(A)_n$—OH wherein R is a linear or branched saturated or unsaturated hydrocarbon chain having from 1 to 20 carbon atoms, preferably from 2 to 15 and more preferably from 2 to 10, or alkyl substituted or non-alkyl substituted aryl group of from 1 to 20 carbon atoms, preferably from 2 to 15 and more preferably from 2 to 10, wherein A is an alkoxy group preferably butoxy, propoxy and/or ethoxy, and n is an integer of from 1 to 5, preferably 1 to 2. Suitable alkoxylated alcohols to be used herein are 1-methoxy-11-dodecanol methoxy propanol, ethoxy propanol and/or propoxy propanol.

Suitable aliphatic or aromatic alcohols to be used herein are according to the formula R—OH wherein R is a linear or branched saturated or unsaturated hydrocarbon chain having from 1 to 20 carbon atoms, preferably from 2 to 15 and more preferably from 2 to 10, or alkyl substituted or non-alkyl substituted aryl group of from 1 to 20 carbon atoms, preferably from 2 to 15 and more preferably from 2 to 10. Suitable aliphatic alcohols to be used herein include linear alcohols like decanol, ethanol and/or propanol. Suitable aromatic alcohol to be used herein is benzyl alcohol.

Suitable glycols to be used herein are according to the formula HO—$(CH_2)_n$—OH wherein n is an integer of 2 to 12. Suitable glycols to be used herein are dodecaneglycol, 1,2-hexanediol and/or propanediol. Preferred hydroxylated solvents for use herein are ethylene glycol butyl ether, propylene glycol butyl ether, diethylene glycol butyl ether, benzyl alcohol, 2-propanol, ethylene glycol ethyl ether or mixtures thereof.

The hydroxylated solvents may typically be present in the microemulsions of the present invention up to a level of 15% by weight, preferably from 0.2% to 12% by weight and more preferably from 0.5% to 10% by weight of the total microemulsion.

The microemulsions of the present invention may comprise as an optional ingredient, other solvents including terpene or mixtures thereof.

Suitable terpenes to be used herein are mono-and bicyclic terpenes, especially those of the hydrocarbon class, which include the terpinenes, terpinolenes and pinenes and mixtures thereof. Highly preferred materials of this type are dipentene, alpha-pinene and/or beta-pinene. For example, pinene is commercially available form SCM Glidco (Jacksonville) under the name Alpha Pinene P&F®.

Terpenes solvents are suitable herein as they contribute to the cleaning performance of the disinfecting microemulsions of the present invention.

Typically, other solvents apart the hydroxylated ones as defined herein above can be present in the microemulsions of the present invention up to a level of 5% by weight of the total microemulsion, preferably from 0.02% to 3% by weight and more preferably from 0.05% to 1.5%.

The microemulsions herein may further comprise a variety of other optional ingredients such as other antimicrobial/antibacterial compounds, chelating agents, radical scavengers, thickeners, builders, buffers, stabilisers, bleach activators, soil suspenders, dye transfer agents, brighteners, anti dusting agents, enzymes, dispersant, dye transfer inhibitors, pigments, perfumes, and dyes. Depending on their respective hydrophilic/hydrophobic character these optional ingredients are present in the aqueous phase and/or in the droplets as defined herein of the microemulsions of the present invention.

The microemulsions of the present invention may comprise as an optional ingredient another antimicrobial/antibacterial compound, or a mixture thereof.

Suitable antimicrobial/antibacterial compounds for use herein include paraben, glutaraldehyde or mixtures thereof.

Typically, the microemulsions of the present invention comprises up to 5% by weight of the total microemulsion of another antibacterial/antimicrobial compound or mixtures thereof, preferably up to 1%.

Suitable radical scavengers for use herein include the well-known substituted mono and di hydroxy benzenes and derivatives thereof, alkyl-and aryl carboxylates and mixtures thereof. Preferred radical scavengers for use herein include di-tert-butyl hydroxy toluene (BHT), p-hydroxy-toluene, hydroquinone (HQ), di-tert-butyl hydroquinone (DTBHQ), mono-tert-butyl hydroquinone (MTBHQ), tert-butyl-hydroxy anysole, p-hydroxy-anysol, benzoic acid, 2,5-dihydroxy benzoic acid, 2,5-dihydroxyterephtalic acid, toluic acid, catechol, t-butyl catechol, 4-allyl-catechol, 4-acetyl catechol, 2-methoxy-phenol, 2-ethoxy-phenol, 2-methoxy4-(2-propenyl)phenol, 3,4-dihydroxy benzaldehyde, 2,3-dihydroxy benzaldehyde, benzylamine, 1,1,3-tris(2-methyl4-hydroxy-5-t-butylphenyl) butane, tert-butyl-hydroxy-anyline, p-hydroxy anyline as well as n-propyl-gallate. Highly preferred for use herein is di-tert-butyl hydroxy toluene, which is for example commercially available from SHELL under the trade name IONOL CP®. These radical scavengers contribute to the stability of the peroxygen bleach-containing microemulsions herein.

Typically, the radical scavenger, or a mixture thereof, is present in the microemulsions of the present invention up to a level of 5% by weight of the total microemulsion, preferably from 0.002% to 3% by weight and more preferably from 0.002% to 1.5%.

Suitable chelating agents to be used herein may be any chelating agent known to those skilled in the art such as the ones selected from the group comprising phosphonate chelating agents, amino carboxylate chelating agents or other carboxylate chelating agents, or polyfunctionally-substituted aromatic chelating agents or mixtures thereof. It has now been found that the addition of a chelating agent in combination with a surfactant on top of an essential oil and/or an active thereof, in the microemulsions of the present invention further improves the disinfecting properties of said microemulsion.

Such phosphonate chelating agents may include etidronic acid (1-hydroxyethylidene-bisphosphonic acid or HEDP) as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, and diethylene triamine penta methylene phosphonates. The phosphonate compounds may be present either in their acid form or as salts of different cations on some or all of their acid functionalities. Preferred phosphonate chelating agents to be used herein are diethylene triamine penta methylene phosphonates. Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy -3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987 to Hartman and Perkins. Ethylenediamine N,N'-disuccinic acid is, for instance, commercially available under the tradename ssEDDS® from Palmer Research Laboratories.

Suitable amino carboxylate chelating agents useful herein include ethylene diamine tetra acetate, diethylene triamine pentaacetate, diethylene triamine pentacetate (DTPA), N-hydroxyethylethylenediamine triacetate, nitrilotri-acetate, ethylenediamine tetraproprionate, triethylenetetraaminehexa-acetate, ethanoldiglycine, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein includes malonic acid, salicylic acid, glycine, aspartic acid, glutamic acid, dipicolinic acid and derivatives thereof, or mixtures thereof.

Typically, the chelating agent, or a mixture thereof, is present in the microemulsions of the present invention at a level of from 0.001% to 5% by weight of the total microemulsion, preferably from 0.002% to 3% by weight and more preferably from 0.002% to 1.5%.

The microemulsions according to the present invention formulated in their liquid form may further comprise as an optional ingredient, a shear thinning polymeric thickener or a mixture thereof.

Such shear thinning polymeric thickeners are suitable herein as they perform a dual function when they are incorporated in the microemulsion according to the present invention, said function being not only to prevent or diminish inhalation by the user of bleach mist/fog when the microemulsion of the present invention is sprayed onto the surface to be disinfected, but also to provide increased contact time of the microemulsion on vertical surfaces, thereby reducing the risk of microemulsion dripping.

Suitable shear thinning polymeric thickeners to be used herein include synthetic and natural occurring polymers. Suitable shear thinning polymeric thickeners for used herein include polyurethane polymers, polyacrylamide polymers, polycarboxylate polymers such as polyacrylic acids and sodium salts thereof, xanthan gum or derivatives thereof, alginate or a derivative thereof, polysaccharide polymers such as substituted cellulose materials like ethoxylated cellulose, carboxymethylcellulose, hydroxymethylcellulose, hydroxypropyl cellulose, hydroxyethyl cellulose and mixtures thereof.

Preferred shear thinning polymeric thickeners for use in the microemulsions of the invention are xanthan gum or derivatives thereof sold by the Kelco Division of Merck under the tradenames KELTROL®, KELZAN AR®, KELZAN D35®, KELZAN S®, KELZAN XZ® and the like.

Xanthan gum is an extra cellular polysaccharide of xanthomonas campestras. Xanthan gum is made by fermentation based on corn sugar or other corn sweetener by-products. Xanthan gum comprises a poly beta-(1→4)-D-Glucopyranosyl backbone chain, similar to that found in cellulose. Aqueous dispersions of xanthan gum and its derivatives exhibit remarkable rheological properties. Xanthan gum exhibits high pseudoplasticity, i.e., over a wide range of concentrations, rapid shear thinning occurs that is generally understood to be instantaneously reversible. Preferred xanthan materials include crosslinked xanthan materials. Xanthan polymers can be crosslinked with a variety of known covalent reacting crosslinking agents reactive with the hydroxyl functionality of large polysaccharide molecules and can also be crosslinked using divalent, trivalent or polyvalent metal ions. Such crosslinked xanthan gels are disclosed in U.S. Pat. No. 4,782,901, which patent is incorporated by reference herein. Suitable crosslinking agents for xanthan materials include metal cations such as Al+3, Fe+3, Sb+3, Zr+4 and other transition metals, etc. Known organic crosslinking agents can also be used. The preferred crosslinked xanthan agent of the invention is KELZAN AR®, a product of Kelco, a division of Merck Incorporated.

The polycarboxylate polymers for use herein preferably have a molecular weight of from 500.000 to 4.500.000, preferably from 1.000.000 to 4.000.000. Most preferred polymers for use herein contain from 0.5% to 4% by weight of a cross-linking agent, wherein the cross-linking agent tends to interconnect linear strands of the polymers to form the resulting cross-linked products. Suitable cross-linking agents include the polyalkenyl polyethers. Polycarboxylate polymers include the polyacrylate polymers. Others monomers besides acrylic acid can be used to form these polymers including such monomers as maleic anhydride which acts as a source of additional carboxylic groups. The molecular weight per carboxylate group of monomers containing a carboxylate group typically varies from 25 to 200, preferably from 50 to 150, more preferably from 75 to 125. Further other monomers may be present in the monomeric mixture, if desired, such as ethylene and propylene which act as diluents.

Preferred polycarboxylate polymers for use herein are the polyacrylate polymers. Commercially available polymers of the polyacrylate type include those sold under the trade names Carbopol®, Acrysol® ICS-1, Polygel®, and Sokalan®. Most preferred polyacrylate polymers are the copolymer of acrylic acid and alkyl ($C_5$–$C_{10}$) acrylate, commercially available under the tradename Carbopol® 1623, Carbopol® 695 from BF Goodrich, and copolymer of acrylic acid and maleic anhydride, commercially available under the tradename Polygel® DB from 3 V Chemical company. Mixtures of any of the polycarboxylate polymers, herein before described, may also be used.

The microemulsions according to the present invention may comprise up to 10% by weight of the total microemulsion of a shear thinning polymeric thickener, or mixtures thereof, preferably from 0.005% to 5% by weight, more preferably from 0.01% to 2% and most preferably from 0.01% to 1%.

No particular mixing order is required to form the oil-in-water microemulsions of the present invention. The microemulsions of the present invention are easily prepared simply by combining all the ingredients in a suitable vessel or container. The order of mixing the ingredients is not particularly important and generally the various ingredients can be added sequentially or all at once. It is not necessary to use elevated temperatures in the formation step and room temperature is sufficient. In a preferred process of making the microemulsions of the present invention an aqueous phase and an oily phase are prepared independently before being mixed together. For example an aqueous phase is prepared by mixing together at least water, a bleach, a surfactant and optional hydrophilic ingredients like chelating agents, buffers and the like, said phase being adjusted to the desired pH. An oily phase is prepared that comprises at least an essential oil/active thereof and optional ingredients like hydroxylated solvents. Then these two phases are mixed together to form the microemulsions of the present invention.

The use of a Microemulsion Comprising Droplets of Essential Oil/Actives for Disinfecting a Surface In its broadest embodiment the present invention encompasses the use of a microemulsion comprising a surfactant, an aqueous phase and droplets dispersed in said aqueous phase, said droplets comprising an essential oil or an active thereof, said droplets having a particle size of less than 100 nanometers, for disinfecting a surface.

The aqueous phase of the microemulsions used according to the present invention comprises at least water. All the ingredients of said microemulsions used to disinfect according to the present invention, i.e., essential oils or actives thereof, surfactants and optional ingredients as well as the levels thereof are as defined herein above.

By "surfaces" it is meant herein any animate surface, e.g., human skin, mouth, teeth as well as any inanimate surface. In a preferred embodiment of the present invention the surfaces to be disinfected with a microemulsion as defined herein, are inanimate surfaces.

These inanimate surfaces include, but are not limited to, hard-surfaces typically found in houses like kitchens, bathrooms, or in car interiors, e.g., tiles, walls, floors, chrome, glass, smooth vinyl, any plastic, plastified wood, table top, sink s, cooker tops, dishes, sanitary fittings such as sinks, showers, shower curtains, wash basins, WCs and the like, as well as fabrics including clothes, curtains, drapes, bed linens, bath linens, table cloths, sleeping bags, tents, upholstered furniture and the like, and carpets. Inanimate surfaces also include household appliances including, but not limited to, refrigerators , freezers, washing machines, automatic dryers, ovens, microwave ovens, dishwashers and so on.

Thus, the present invention also encompasses a process of disinfecting a fabric, as the inanimate surface. In such a process a microemulsion, as defined herein, is contacted with the fabrics to be disinfected. This can be done either in a so-called "pretreatment mode", where a microemulsion, as defined herein, is applied neat onto said fabrics before the fabrics are rinsed, or washed then rinsed, or in a "soaking mode" where a microemulsion, as defined herein, is first diluted in an aqueous bath and the fabrics are immersed and soaked in the bath, before they are rinsed, or in a "through the wash mode", where a microemulsion, as defined herein, is added on top of a wash liquor formed by dissolution or dispersion of a typical laundry detergent.

In the pretreatment mode, it has been found that it is highly preferred that the fabrics be rinsed after they have been contacted with a microemulsion, as defined herein, before said microemulsion has completely dried off, especially in the embodiment herein wherein the microemulsion used comprises a bleach like a peroxygen bleach. Indeed, it has been found that water evaporation contributes to increase the concentration of free radicals onto the surface of the fabrics and, consequently, the rate of chain reaction. Indeed, free radicals typically result from the decomposition of bleach that may be catalysed due to the presence of metal ions on the surface of a fabric and/or to the exposure of the fabrics to UV radiation from sunlight. It is also speculated that an auto-oxidation reaction occurs upon evaporation of water when such microemulsions containing a bleach are left to dry onto the fabrics. For example said reaction of auto-oxidation generates peroxy-radicals which may contribute to the degradation of cellulose. Thus, not leaving such a bleach-containing microemulsions to dry onto the fabric, in a process of pretreating fabrics, contributes to reduce the tensile strength loss when pretreating fabrics with such products.

In the pretreatment mode, the process comprises the steps of applying a microemulsion, as defined herein, neat onto said fabrics, or at least infected portions thereof (i.e., directly applying said liquid microemulsion, as defined herein onto said fabrics without undergoing any dilution), and subsequently rinsing, or washing then rinsing said fabrics. In this mode, the neat microemulsion can optionally be left to act onto said fabrics for a period of time ranging from 1 min. to 1 hour, preferably from 1 minute to 30 minutes, before the fabrics are rinsed, or washed then rinsed, provided that in the embodiment of the present invention wherein said microemulsion comprises a peroxygen bleach it is not left to dry onto said fabrics. For particularly though stains, it may be appropriate to further rub or brush said fabrics by means of a sponge or a brush, or by rubbing two pieces of fabrics against each other.

In another mode, generally referred to as "soaking", the process comprises the steps of diluting a microemulsion as defined herein, in an aqueous bath so as to form a diluted composition. The dilution level of said microemulsion, in an aqueous bath is typically up to 1:85, preferably up to 1:50 and more preferably about 1:25 (microemulsion:water). The fabrics are then contacted with the aqueous bath comprising the microemulsion, and the fabrics are finally rinsed, or washed then rinsed. Preferably in that embodiment, the fabrics are immersed in the aqueous bath comprising the microemulsion, and also preferably, the fabrics are left to soak therein for a period of time ranging from 1 minute to 48 hours, and preferably from 3 minutes to 24 hours.

In yet another mode which can be considered as a sub-embodiment of "soaking", generally referred to as "through the wash mode", the microemulsion, as defined herein, is used as a so-called laundry additive. And in that embodiment the aqueous bath is formed by dissolving or dispersing a conventional laundry detergent in water. The microemulsion is contacted with the aqueous bath, and the fabrics are then contacted with the aqueous bath containing the microemulsion. Finally, the fabrics are rinsed.

In another embodiment the present invention also encompasses a process of disinfecting a hard-surface, as the inanimate surface. In such a process a microemulsion, as defined herein, is contacted with the hard-surfaces to be disinfected. Thus, the present invention also encompasses a process of disinfecting a hard-surface with a microemulsion, as defined herein, wherein said process comprises the step of applying said microemulsion to said hard-surface, preferably only infected portions thereof, and optionally rinsing said hard-surface.

In the process of disinfecting hard-surfaces according to the present invention the microemulsion, as defined herein, may be applied to the surface to be disinfected in its neat form or in its diluted form typically up to 200 times their weight of water, preferably into 80 to 2 times their weight of water, and more preferably 60 to 2 times.

In the preferred embodiment of the process of the present invention wherein said liquid microemulsion is applied to a hard-surface to be disinfected in its diluted form, it is not necessary to rinse the surface after the microemulsion has been applied, indeed no visible residues are left onto the surface.

Packaging Form of the Microemulsions

The microemulsions herein may be packaged in a variety of suitable detergent packaging known to those skilled in the art. The microemulsions herein may desirably be packaged in manually operated spray dispensing containers, which are usually made of synthetic organic polymeric plastic materials. Accordingly, the present invention also encompasses microemulsions as described herein before packaged in a spray dispenser, preferably in a trigger spray dispenser or in a pump spray dispenser.

For example, said spray-type dispensers allow to uniformly apply to a relatively large area of a surface to be disinfected, the microemulsions of the present invention, thereby contributing to disinfecting properties of said microemulsions. Such spray-type dispensers are particularly suitable to treat vertical surfaces.

Suitable spray-type dispensers to be used according to the present invention include manually operated foam trigger-type dispensers sold for example by Specialty Packaging Products, Inc. or Continental Sprayers, Inc. These types of dispensers are disclosed, for instance, in U.S. Pat. No. 4,701,311 to Dunnining et al. and U.S. Pat. No. 4,646,973 and U.S. Pat. No. 4,538,745 both to Focarracci. Particularly preferred to be used herein are spray-type dispensers such as T 8500® commercially available from Continental Sprayers International, T8900® commercially available from Continental Sprayers Int., or T 8100® commercially available from Canyon, Northern Ireland. In such a dispenser the microemulsion is divided in fine liquid droplets resulting in a spray that is directed onto the surface to be treated. Indeed, in such a spray-type dispenser the microemulsion contained in the body of said dispenser is directed through the spray-type dispenser head via energy communicated to a pumping mechanism by the user as said user activates said pumping mechanism. More particularly, in said spray-type dispenser head the microemulsion is forced against an obstacle, e.g. a grid or a cone or the like, thereby providing shocks to help atomise the microemulsion, i.e. to help the formation of the spray form of the microemulsion.

The microemulsions of the present invention may also be executed in the form of wipes. By "wipes" it is meant herein disposable towels incorporating a microemulsion according to the present invention. Preferably said wipes are packaged in a plastic box. Accordingly, the present invention also encompasses wipes, e.g., disposable paper towels, impregnated/wetted with a microemulsion as described herein before. The advantage of this execution is a faster usage of a disinfecting microemulsion by the user, this even outside the house, i.e. there is no need to pour the liquid microemulsions according to the present invention on the surfaces to be disinfected and to dry it out with a cloth. In other words, wipes allow disinfecting of surfaces in one step.

The present invention will be further illustrated by the following examples.

EXAMPLE

The following microemulsions were made by mixing the listed ingredients in the listed proportions (weight % unless otherwise specified).

| Microemulsions (weight %) | I | II | III | IV | V | VI |
|---|---|---|---|---|---|---|
| Hydrogen peroxide | 3.0 | 3.0 | 5.8 | 3.0 | 1.0 | 3.0 |
| Betaine* | 0.1 | 0.1 | 1.5 | 0.1 | 0.05 | 0.2 |
| C10 amine oxide | 1.8 | 1.8 | 3.0 | 1.8 | 0.9 | 3.0 |
| Geraniol | 0.3 | 0.3 | 0.3 | 0.3 | — | 0.2 |
| Thymol | — | — | — | — | 0.05 | 0.1 |
| Eugenol | — | — | 0.1 | — | — | — |
| Eucalyptol | 0.1 | 0.1 | — | 0.1 | 0.1 | — |
| Butyl carbitol ® | 2.0 | 2.0 | — | 2.0 | 1.5 | 1.0 |
| Dobanol 91-10 ® | 0.5 | 1.5 | 1.6 | 1.5 | — | 1.2 |
| Dobanol 23-3 ® | — | 0.6 | 1.1 | 0.6 | — | — |
| Benzyl alcohol | 2.0 | 2.0 | — | 2.0 | 0.1 | — |
| Limonene | 0.2 | 0.2 | — | 0.2 | 0.1 | — |
| Isopropanol | — | — | — | — | 1.0 | 1.0 |
| Water and minors H$_2$SO$_4$ up to pH 4 | | | up to 100% | | | |

Betaine * is either coconut betaine commercially available from Seppic under the trade name Amonyl 265 ® or laurylbetaine commercially available from Albright & Wilson under the trade name Empigen BB/L ® or mixtures thereof.
Butyl carbitol ® is diethylene glycol butyl ether
Dobanol 91-10 ® is nonionic surfactant having an aliphatic chain of C9–C11 and an ethoxylation of 10 available from Shell
Dobanol 23-3 ® is nonionic surfactant having an aliphatic chain of C12–C13 and an ethoxylation of 3 available from Shell.

| Microemulsions (weight %) | VII | VIII | IX | X | XI | XII |
|---|---|---|---|---|---|---|
| Hydrogen peroxide | 2.0 | 2.0 | 3.0 | 1.0 | 1.0 | 1.0 |
| Betaine* | 1.5 | 1.0 | 1.0 | 1.0 | 0.2 | 0.1 |
| Lauryl amine oxide | 1.0 | 1.0 | 3.0 | 3.0 | 3.0 | 2.0 |
| Thymol | — | 0.1 | — | — | — | — |
| Geraniol | — | 0.05 | 0.1 | — | — | — |
| Eucalyptol | — | 0.05 | — | — | — | — |
| Ethyl paraben | — | — | — | — | 0.4 | 0.4 |
| Eugenol | — | — | — | — | — | 0.2 |
| Dobanol 91-10 ® | 0.5 | 0.5 | 0.3 | 0.3 | 0.8 | 0.1 |
| HEDP | 0.1 | — | 0.1 | 0.05 | 0.2 | 0.3 |
| ATMP | — | 0.1 | — | — | — | — |
| BHT | 0.1 | 0.1 | 0.05 | 0.05 | 0.08 | 0.08 |
| Tetraborate | 0.5 | 0.5 | 0.7 | 0.7 | 1.0 | 1.0 |
| Water and minors NaOH up to pH 8.5 | | | up to 100% | | | |

HEDP is etidronic acid.
ATMP is nitrilotris(methylene)triphosphonic acid.
BHT is tert-butyl hydroxy toluene.
Tetraborate is sodium tetraborate decahydrate.

These microemulsions are according to the present invention, i.e. that they comprise droplets comprising essential oils/actives, said droplet having a particle size of less than 100 nm, when the microemulsions are both in their neat form or diluted form.

These microemulsions passed the prEN 1040 test of the European committee of standardisation. Indeed, these microemulsions provide excellent disinfection when used neat or diluted, e.g. at 1:100, 1:25, 1:50 dilution levels.

What is claimed is:
1. A composition in the form of a microemulsion suitable for disinfecting surfaces, said composition comprising:
   a) an aqueous phase which comprises:
      i) from 0.01% to 40% by weight, of a surfactant, wherein said surfactant is a betaine surfactant, an N-oxide surfactant, and mixtures thereof;
      ii) from 0.001% to 15% by weight, of a peroxygen bleaching system;
      iii) from 0.002% to 3% by weight, of a radical scavenger;
      iv) the balance water; and
   b) a non-aqueous phase which comprises:
      i) from 0.005% to 5% by weight, of an essential oils, said essential oils are obtained from sources selected from the group consisting of thyme, lemon grass, lemons, oranges, anise, clove, cinnamon, geraniums, roses, mint, lavender, eucalyptus, citronella, peppermint, camphor, sandalwood, cedar, and mixtures thereof;
      ii) the balance one or more hydroxylated solvents, said solvents selected from the group consisting of 2-hexyloxyethanol, ethyleneglycol ethyl ether, ethyleneglycol butyl ether, n-butoxypropyloxypropanol, butyl triglycol ether, butyl diglycol ether, diethyleneglycol butyl ether, 2-(2-butoxyethoxy)-ethanol, 2-(2-propoxyethoxy) propanol, 2-ethyl,-1,3-hexanediol, 2,2,4-trimethyl-1,3-pentanediol, 1,6-hexanediol, and mixtures thereof.

2. A composition according to claim 1 wherein said bleach is hydrogen peroxide.

3. A composition according to claim 2 wherein said essential oil comprises a terpene selected from the group consisting of geraniol, thymol, eugenol, eucalyptol, and mixtures thereof.

4. A composition according to claim 1 wherein said betaine surfactant has the formula:

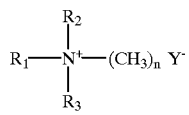

wherein R$_1$ is a hydrocarbon chain containing from 1 to 24 carbon atoms, R$_2$ and R$_3$ independently contain from 1 to 3 carbon atoms, the index n is an integer from 1 to 10, Y is selected from carboxyl, sulfonyl, or mixtures thereof, and the sum of the number of carbon atoms in R$_1$, R$_2$ and R$_3$ is from 14 to 24.

5. A composition according to claim 4 wherein said index n has the value of 1.

6. A composition according to claim 1 comprising from 0.05% to 15% by weight of a surfactant.

7. A composition according to claim 6 comprising from 0.1% to 12% by weight of a surfactant.

8. A composition according to claim 1 wherein said bleach is selected from the group consisting of hydrogen peroxide, percarbonates, persilicates, persulphates, perborates, peroxyacids, hydroperoxides, aromatic diacyl peroxides, aromatic diacyl peroxides, and mixtures thereof.

9. A composition according to claim 1 comprising from 0.1% to 10% by weight, of said peroxygen bleach.

10. A composition according to claim 9 comprising from 0.2% to 5% by weight, of said peroxygen bleach.

11. A composition according to claim 1 comprising from 0.002% to 1.5% by weight, of a free radical scavenger.

12. A composition according to claim 1 wherein said free radical scavenger is selected from the group consisting of di-tert-butyl hydroxytoluene, p-hydroxytoluene, hydroquinone, di-tert-butyl hydroquinone, mono-tert-butyl-hydroquinone, tert-butyl-hydroxyanisole, p-hydroxyanisole, benzoic acid, 2,5-dihydroxyterephtalic acid, toluic acid, catechol, t-butyl catechol, 4-allyl-catechol, 4-acetyl-catechol, 2-methoxyphenol, 2-ethoxyphenol, 2-methoxy-4-(2-propenyl)phenol, 3,4-dihydroxybenzaldehyde, 2,3-dihydroxybenzaldehyde, benzylamine, 1,1,2-tris(2-methyl-4-hydroxy-5-t-butylphenyl)butane, and mixtures thereof.

13. A composition according to claim 1 comprising from 0.006% to 3% by weight, of said essential oil.

14. A composition according to claim 13 comprising from 0.05% to 1% by weight, of said essential oil.

15. A composition according to claim 6 wherein said aqueous phase further comprises from 0.005% to 5% by weight, of a shear thinning polymeric thickener.

16. A composition according to claim 6 wherein said aqueous phase further comprises from 0.01% to 2% by weight, of a shear thinning polymeric thickener.

17. A composition according to claim 16 wherein said aqueous phase further comprises from 0.01% to 1% by weight, of a shear thinning polymeric thickener.

* * * * *

UNITED STATES PATENT AND TRADEMARK OFFICE
CERTIFICATE OF CORRECTION

PATENT NO. : 6,114,298
DATED : September 5, 2000
INVENTOR(S) : Marco Petri et al.

It is certified that error appears in the above-identified patent and that said Letters Patent is hereby corrected as shown below:

Column 20, line 3, claim 15., should read -- A composition according to claim 1 -- . . .
Column 20, line 6, claim 16., should read -- A composition according to claim 1 -- . . .

Signed and Sealed this

Seventeenth Day of April, 2001

Attest:

NICHOLAS P. GODICI

Attesting Officer     *Acting Director of the United States Patent and Trademark Office*